(12) United States Patent
Dakka et al.

(10) Patent No.: US 9,272,974 B2
(45) Date of Patent: *Mar. 1, 2016

(54) PROCESS FOR PRODUCING PHENOL AND/OR CYCLOHEXANONE FROM CYCLOHEXYLBENZENE

(71) Applicant: ExxonMobil Chemical Patents Inc., Baytown, TX (US)

(72) Inventors: Jihad M. Dakka, Whitehouse Station, NJ (US); Charles Morris Smith, Princeton, NJ (US); Christopher L. Becker, Manhattan, KS (US); Terry E. Helton, Montgomery, TX (US); Jason D. Davis, Humble, TX (US); Edmund J. Mozeleski, Somerset, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/420,085

(22) PCT Filed: Sep. 11, 2013

(86) PCT No.: PCT/US2013/059191
§ 371 (c)(1),
(2) Date: Feb. 6, 2015

(87) PCT Pub. No.: WO2014/043188
PCT Pub. Date: Mar. 20, 2014

(65) Prior Publication Data
US 2015/0203429 A1 Jul. 23, 2015

Related U.S. Application Data

(60) Provisional application No. 61/701,984, filed on Sep. 17, 2012.

(30) Foreign Application Priority Data

Nov. 19, 2012 (EP) ...................... 1219133

(51) Int. Cl.
| | |
|---|---|
| C07C 45/53 | (2006.01) |
| C07C 37/08 | (2006.01) |
| C07C 2/66 | (2006.01) |
| C07C 407/00 | (2006.01) |
| C07C 1/24 | (2006.01) |
| C07C 2/74 | (2006.01) |
| C07C 5/03 | (2006.01) |

(52) U.S. Cl.
CPC . *C07C 45/53* (2013.01); *C07C 1/24* (2013.01); *C07C 2/74* (2013.01); *C07C 5/03* (2013.01); *C07C 37/08* (2013.01); *C07C 407/00* (2013.01); *C07C 2101/14* (2013.01); *C07C 2101/16* (2013.01); *C07C 2529/08* (2013.01); *C07C 2529/12* (2013.01); *C07C 2529/70* (2013.01); *C07C 2529/74* (2013.01)

(58) Field of Classification Search
CPC ............ C07C 45/53; C07C 37/08; C07C 2/66
USPC ........................ 568/376, 798, 799; 585/467
See application file for complete search history.

(56) References Cited

U.S. PATENT DOCUMENTS

| | | | | |
|---|---|---|---|---|
| 4,439,409 | A | * | 3/1984 | Puppe et al. ................. 423/706 |
| 4,954,325 | A | * | 9/1990 | Rubin et al. ................. 423/706 |
| 5,250,277 | A | * | 10/1993 | Kresge et al. .............. 423/329.1 |
| 6,037,513 | A | | 3/2000 | Chang et al. |
| 6,720,462 | B2 | | 4/2004 | Kuhnle et al. |
| 6,852,893 | B2 | | 2/2005 | Kuhnle et al. |
| 2002/0169331 | A1 | | 11/2002 | Miura et al. |
| 2007/0265476 | A1 | | 11/2007 | Dakka et al. |
| 2008/0033217 | A1 | | 2/2008 | Dakka et al. |
| 2008/0086018 | A1 | | 4/2008 | Cheng et al. |
| 2008/0154082 | A1 | | 6/2008 | Dandekar et al. |
| 2009/0187047 | A1 | | 7/2009 | Dakka et al. |
| 2009/0306433 | A1 | | 12/2009 | Dakka et al. |
| 2009/0312580 | A1 | | 12/2009 | Cheng et al. |
| 2011/0190543 | A1 | | 8/2011 | Dakka et al. |

FOREIGN PATENT DOCUMENTS

| | | |
|---|---|---|
| CN | 101 560 396 | 7/2012 |
| WO | WO 2007/093357 | 8/2007 |
| WO | WO 2007/093359 | 8/2007 |
| WO | WO 2008/101616 | 8/2008 |
| WO | WO 2009/131769 | 10/2009 |
| WO | WO 2010/098916 | 9/2010 |

OTHER PUBLICATIONS

U.S. Appl. No. 60/601,755, filed Aug. 13, 2004, Smith et al.

* cited by examiner

*Primary Examiner* — Sikarl Witherspoon
(74) *Attorney, Agent, or Firm* — Siwen Chen; Stephen A. Baehl

(57) ABSTRACT

In a process for producing phenol and/or cyclohexanone, cyclohexylbenzene is contacted with an oxygen-containing gas to produce an oxidation effluent containing cyclohexylbenzene hydroperoxide and the cyclohexylbenzene hydroperoxide is then contacted with a cleavage catalyst to produce a cleavage effluent containing phenol and cyclohexanone. At least one of the oxidation effluent and the cleavage effluent also contains at least one by-product selected from phenylcyclohexanols and phenylcyclohexanones and the process further comprises contacting the by-product with a dehydration catalyst to convert the by-product to phenylcyclohexene and hydrogenating the phenylcyclohexene to cyclohexylbenzene. The dealkylation and hydrogenation may be conducted in a single stage.

21 Claims, 3 Drawing Sheets

PROCESS FOR PRODUCING PHENOL AND/OR CYCLOHEXANONE FROM CYCLOHEXYLBENZENE

PRIORITY CLAIM

This application is a National Stage Application of International Application No. PCT/US2013/059191, filed Sep. 11, 2013, which claims the benefit of U.S. Provisional Application No. 61/701,984, filed Sep. 17, 2012, and European Application No. 12193133.1, filed Nov. 19, 2012, the disclosures of which are fully incorporated herein by their reference.

FIELD

The present invention relates to a process for producing phenol.

BACKGROUND

Phenol is an important product in the chemical industry and is useful in, for example, the production of phenolic resins, bisphenol A, ε-caprolactam, adipic acid, and plasticizers.

Currently, the most common route for the production of phenol is the Hock process via cumene. This is a three-step process in which the first step involves alkylation of benzene with propylene in the presence of an acidic catalyst to produce cumene. The second step is oxidation, preferably aerobic oxidation, of the cumene to the corresponding cumene hydroperoxide. The third step is the cleavage of the cumene hydroperoxide in the presence of heterogeneous or homogenous catalysts into equimolar amounts of phenol and acetone, a co-product. However, the world demand for phenol is growing more rapidly than that for the acetone co-product. In addition, due to developing shortages in supply, the cost of propylene is likely to increase.

Thus, a process that avoids or reduces the use of propylene as a feed and coproduces higher ketones, rather than acetone, may be an attractive alternative route to the production of phenol. For example, there is a growing market for cyclohexanone, which is used as an industrial solvent, as an activator in oxidation reactions and in the production of adipic acid, cyclohexanone resins, cyclohexanone oxime, caprolactam, and nylon 6.

It is known that phenol and cyclohexanone can be co-produced by a variation of the Hock process in which cyclohexylbenzene is oxidized to obtain cyclohexylbenzene hydroperoxide, and the hydroperoxide is decomposed in the presence of an acid catalyst to the desired phenol and cyclohexanone. Although various methods are available for the production of cyclohexylbenzene, a preferred route is via benzene hydroalkylation in which benzene is contacted with hydrogen in the presence of a catalyst such that part of the benzene is converted into cyclohexene which then reacts with the remaining benzene to produce the desired cyclohexylbenzene. One such method is disclosed in U.S. Pat. No. 6,037,513, in which the catalyst comprises a molecular sieve of the MCM-22 family and at least one hydrogenation metal selected from palladium, ruthenium, nickel, cobalt, and mixtures thereof. The '513 patent also discloses that the resultant cyclohexylbenzene can be oxidized to the corresponding hydroperoxide which is then decomposed to the desired phenol and cyclohexanone co-product in roughly equimolar amounts.

However, the oxidation step leads to the production of non-negligible amounts of by-products, including phenylcyclohexanols and phenylcyclohexanones. To improve the process, the phenylcyclohexanols and phenylcyclohexanones are preferably converted to useful products.

SUMMARY

It has now been found that the phenylcyclohexanols and phenylcyclohexanones produced as by-products of cyclohexylbenzene oxidation can be converted to cyclohexylbenzene by a combination of dehydration and hydrogenation. In this way, product yield is improved. In addition, by effecting the conversion in the presence of co-fed hydrogen with an acid catalyst containing a hydrogenating metal component, the dehydration and hydrogenation can be achieved in a single step. This reduces potential side reactions of the phenylcyclohexene intermediate, thereby improving catalyst selectivity and stability.

In one aspect, the invention resides in a process for producing phenol and/or cyclohexanone, said process comprising:

(a) contacting cyclohexylbenzene with an oxygen-containing gas under conditions effective to produce an oxidation effluent containing cyclohexylbenzene hydroperoxide;

(b) contacting at least part of said oxidation effluent containing cyclohexylbenzene hydroperoxide with a cleavage catalyst under conditions effective to produce a cleavage effluent containing phenol and cyclohexanone;

wherein at least one of said oxidation effluent and said cleavage effluent contains at least one by-product selected from phenylcyclohexanols and phenylcyclohexanones;

(c) contacting at least part of said at least one effluent containing said at least one by-product with a dehydration catalyst under conditions effective to convert at least part of said by-product to phenylcyclohexene; and (d) contacting at least part of said phenylcyclohexene with hydrogen under conditions effective to convert at least part of said phenylcyclohexene to cyclohexylbenzene.

In one embodiment, the contacting steps (c) and (d) are conducted in the same reaction zone, desirably in the presence of a bifunctional catalyst comprising an acid (such as a solid acid) dehydration component and a hydrogenating metal component. In certain embodiments, the solid acid dehydration component comprises a molecular sieve, such as an MCM-22 family zeolite, and the said hydrogenating metal component comprises at least one metal selected from Groups 6 to 12 of the Periodic Table of Elements, such as palladium.

Conveniently, the conditions in the contacting steps (c) and (d) comprise a temperature of 25° C. to 200° C. and the conditions in the contacting step (d) further comprise a hydrogen partial pressure of 15 kPa to 1000 kPa.

In certain embodiments, the process further comprises:

(e) separating said cleavage effluent from said contacting step (b) into a first fraction containing phenol and cyclohexanone and a second fraction containing said at least one by-product; and (f) supplying said second fraction to said contacting step (c).

Desirably, the contacting step (a) is effected in the presence of a catalyst, especially a cyclic imide catalyst.

In certain embodiments, the cyclohexylbenzene is produced by a reaction of benzene with hydrogen in the presence of a hydroalkylation catalyst, desirably comprising a solid acid alkylation component, such as an MCM-22 family zeolite, and a hydrogenating metal component.

A second aspect of the invention resides in a process for producing phenol and/or cyclohexanone, said process comprising:

(I) contacting benzene with hydrogen in the presence of a hydroalkylation catalyst under a hydroalkylation condition effective to produce a hydroalkylation effluent comprising cyclohexylbenzene;

(II) contacting at least part of said cyclohexylbenzene in said hydroalkylation effluent with an oxygen-containing gas under conditions effective to produce an oxidation effluent containing cyclohexylbenzene hydroperoxide;

(III) contacting at least part of said oxidation effluent containing cyclohexylbenzene hydroperoxide with a cleavage catalyst under conditions effective to produce a cleavage effluent containing phenol and cyclohexanone, wherein at least one of said oxidation effluent and said cleavage effluent contains at least one by-product selected from phenylcyclohexanols and phenylcyclohexanones;

(IV) contacting at least part of said at least one effluent containing said at least one by-product with a dehydration catalyst under conditions effective to convert at least part of said by-product to phenylcyclohexene; and (V) contacting at least part of said phenylcyclohexene with hydrogen under conditions effective to convert at least part of said phenylcyclohexene to cyclohexylbenzene.

DETAILED DESCRIPTION OF THE EMBODIMENTS

Figure 1:
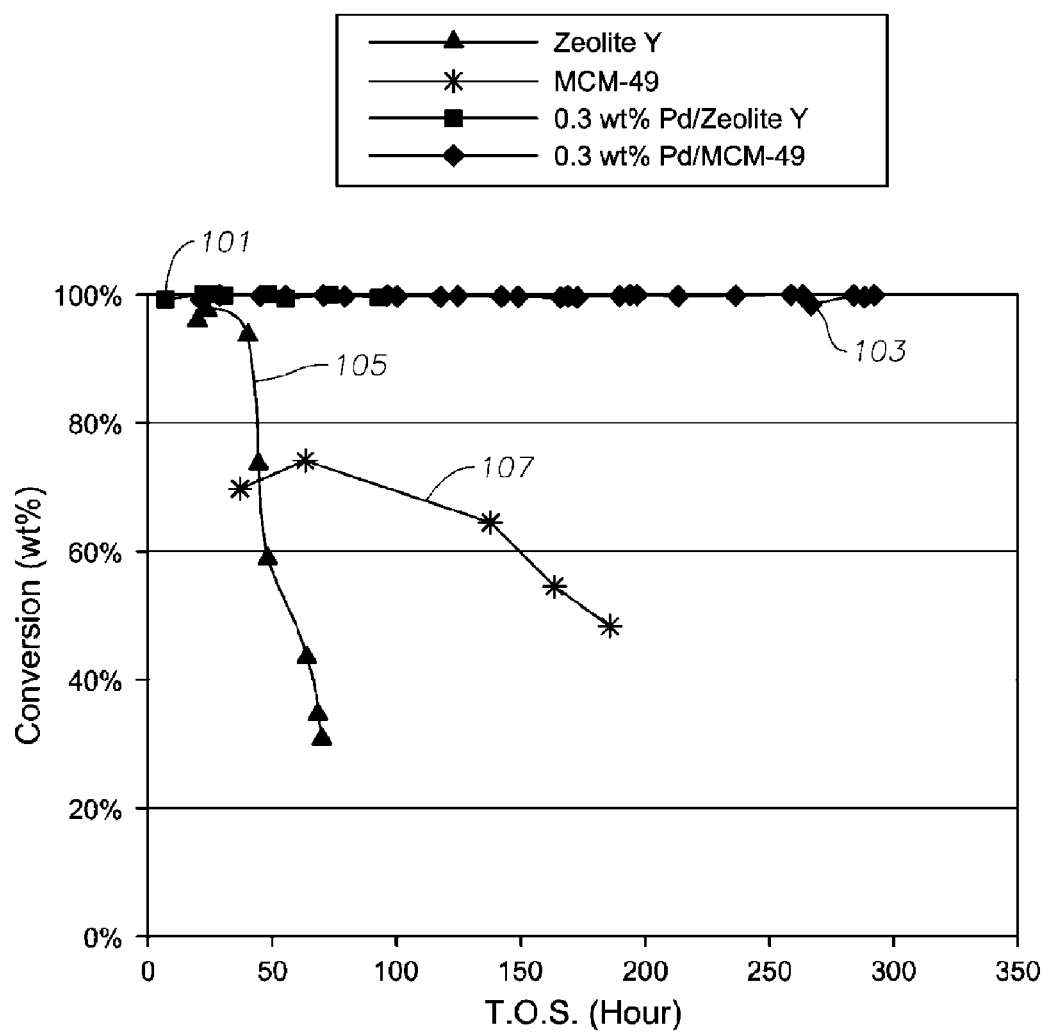
FIG. 1 is a graph comparing phenylcyclohexanol conversion against time on stream for the processes of Examples 1 to 4.

In the present disclosure, a process may be described as comprising at least one "step." It should be understood that each step is an action or operation that may be carried out once or multiple times in the process, in a continuous or discontinuous fashion. Unless specified to the contrary or the context clearly indicates otherwise, each step in a process may be conducted sequentially in the order as they are listed, with or without overlapping with one or more other step, or in any other order, as the case may be. In addition, some steps may be conducted simultaneously, for example, in the same reaction zone.

Unless otherwise indicated, all numbers in the present disclosure are to be understood as being modified by the term "about" in all instances. It should also be understood that the precise numerical values used in the specification and claims constitute specific embodiments. Efforts have been made to ensure the accuracy of the data in the examples. However, it should be understood that any measured data inherently contains a certain level of error due to the limitation of the technique and equipment used for making the measurement.

As used herein, the indefinite article "a" or "an" shall mean "at least one" unless specified to the contrary or the context clearly indicates otherwise. Thus, embodiments using "a hydrogenating metal" include embodiments where one, two or more hydrogenating metals are used, unless specified to the contrary or the context clearly indicates that only one hydrogenating metal is used. Likewise, "an oxygenated hydrocarbon" should be interpreted to include one or more types of hydrogenated hydrocarbon at various concentrations unless specified or indicated by the context to mean only one specific type of hydrogenated hydrocarbon.

As used herein, the term "cyclohexylbenzene" shall mean benzene substituted by a single cyclohexyl group, unless specified to the contrary or the context clearly indicates otherwise. As used herein, the generic term "dicyclohexylbenzene" shall include 1,2-dicyclohexylbenzene, 1,3-dicyclohexylbenzne, 1,4-dicyclohexylbenzene, and mixtures and combinations of at least two thereof in any proportion. As used herein, the generic term "tricyclohexylbenzene" shall include 1,2,3-tricyclohexylbenzene, 1,2,4-tricyclohexylbenzene and 1,3,5-tricyclohexylbenzene, and combinations and mixtures thereof at any proportion. The generic term "polycycloyhexylbenzene" shall include any of the dicyclohexylbenzene isomers and tricyclohexylbenzene isomers described above, and combinations and mixtures of at least two thereof in any proportion.

A process is described herein for producing phenol and/or cyclohexanone from cyclohexylbenzene. In the process, cyclohexylbenzene is initially oxidized to produce cyclohexylbenzene hydroperoxide, which can then be cleaved to generate the desired phenol and cyclohexanone. However, the oxidation step also produces by-products, including phenylcyclohexanols and phenylcyclohexanones, which in the present process are converted to cyclohexylbenzene by a combination of dehydration and hydrogenation. These combined dehydration and hydrogenation steps are preferably conducted in a single reactor by contacting the phenylcyclohexanols and phenylcyclohexanones with hydrogen in the presence of a solid acid catalyst containing a hydrogenating metal component. The resultant cyclohexylbenzene can then be recycled to the oxidation step to improve product yield.

In one preferred embodiment, the present process form part of an integrated process for producing phenol from benzene in which the benzene is initially alkylated or hydroalkylated to produce the cyclohexylbenzene feed to the present process. The ensuing description will therefore focus on this integrated process.

Production of Cyclohexylbenzene

The cyclohexylbenzene starting material for the present process can be produced by the alkylation of benzene with cyclohexene according to the following reaction:

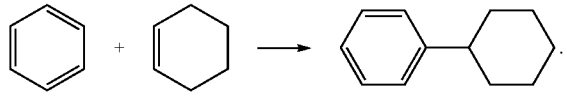 [SMILES: c1ccccc1 ; C1=CCCCC1 ; c1ccc(C2CCCCC2)cc1]

The cyclohexene can be supplied to the reaction zone as a separate feed from the benzene, but normally is produced in situ by the selective hydrogenation of benzene in the presence of a bifunctional catalyst. In the case of cyclohexene being produced by in-situ hydrogenation of benzene, the combined reaction is generally termed "hydroalkylation" and may be summarized as follows:

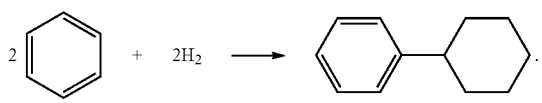

Any commercially available benzene feed can be used in the hydroalkylation step, but preferably the benzene has a purity level of at least 99 wt %. Similarly, although the source of hydrogen is not critical, it is desirable in certain embodiments that the hydrogen is at least 99 wt % pure.

Conveniently, the total feed to the hydroalkylation step contains less than 1000 ppm, such as less than 500 ppm, for example less than 100 ppm, water. In addition, the total feed desirably contains less than 100 ppm, such as less than 30 ppm, for example less than 3 ppm, sulfur and less than 10 ppm, such as less than 1 ppm, for example less than 0.1 ppm, nitrogen.

Hydrogen can be supplied to the hydroalkylation step over a wide range of values, but desirably is arranged such that the molar ratio of hydrogen to benzene in the hydroalkylation feed is from about 0.15:1 to about 15:1, such as from about 0.4:1 to about 4:1, for example from about 0.4 to about 0.9:1.

In addition to the benzene and hydrogen, a diluent, which is substantially inert under hydroalkylation conditions, may be supplied to the hydroalkylation reaction. Desirably the diluent is a hydrocarbon, in which the desired cycloalkylaromatic product, in this case cyclohexylbenzene, is soluble, such as a straight chain paraffinic hydrocarbon, a branched chain paraffinic hydrocarbon, and/or a cyclic paraffinic hydrocarbon. Examples of suitable diluents are decane and cyclohexane. Cyclohexane is a particularly attractive diluent since it is an unwanted by-product of the hydroalkylation reaction.

Although the amount of diluent is not narrowly defined, desirably the diluent is added in an amount such that the weight ratio of the diluent to the aromatic compound is at least 1:100, for example at least 1:10, but no more than 10:1, desirably no more than 4:1.

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. Suitable reaction temperatures are from about 100° C. to about 400° C., such as from about 125° C. to about 250° C., while suitable reaction pressures are from about 100 kPa to about 7,000 kPa, such as from about 500 kPa to about 5,000 kPa.

The catalyst employed in the hydroalkylation reaction is a bifunctional catalyst comprising a hydrogenating metal component and an alkylating solid acid component. In certain embodiments, the alkylating solid acid component comprises a molecular sieve of the MCM-22 family. The term "MCM-22 family material" (or "material of the MCM-22 family" or "molecular sieve of the MCM-22 family"), as used herein, includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of MCM-22 family generally have an X-ray diffraction pattern including d-spacing maxima at 12.4±0.25, 6.9±0.15, 3.57±0.07, and 3.42±0.07 Angstrom. The X-ray diffraction data used to characterize the material are obtained by standard techniques using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof. Preferably, the molecular sieve is selected from (a) MCM-49; (b) MCM-56; and (c) isotypes of MCM-49 and MCM-56, such as ITQ-2.

Any known hydrogenating metal can be employed in the hydroalkylation catalyst, although suitable metals include palladium, ruthenium, nickel, zinc, tin, and cobalt, with palladium being particularly advantageous. In certain embodiments, the amount of hydrogenating metal present in the catalyst is from about 0.05 wt % to about 10 wt %, such as from about 0.1 wt % to about 5 wt %, of the catalyst. In one embodiment, where the MCM-22 family molecular sieve is an aluminosilicate, the amount of hydrogenating metal present is such that the molar ratio of the aluminum in the molecular sieve to the hydrogenating metal is from about 1.5 to about 1500, for example from about 75 to about 750, such as from about 100 to about 300.

The hydrogenating metal may be directly supported on the MCM-22 family molecular sieve by, for example, impregnation or ion exchange. However, in a more preferred embodiment, at least 50 wt %, for example at least 75 wt %, and in certain embodiments substantially all of the hydrogenating metal is supported on an inorganic oxide separate from but composited with the molecular sieve. In particular, it is found that by supporting the hydrogenating metal on the inorganic oxide, the activity of the catalyst and its selectivity to cyclohexylbenzene and dicyclohexylbenzene are increased as compared with an equivalent catalyst in which the hydrogenating metal is supported on the molecular sieve.

The inorganic oxide employed in such a composite hydroalkylation catalyst is not narrowly defined provided it is stable and inert under the conditions of the hydroalkylation reaction. Suitable inorganic oxides include oxides of Groups 2, 4, 13, and 14 of the Periodic Table of Elements, such as alumina, titania, and/or zirconia. As used herein, the numbering scheme for the Periodic Table Groups is as disclosed in Chemical and Engineering News, 63(5), 27 (1985).

The hydrogenating metal is deposited on the inorganic oxide, conveniently by impregnation, before the metal-containing inorganic oxide is composited with the molecular sieve. Desirably, the catalyst composite is produced by co-pelletization, in which a mixture of the molecular sieve and the metal-containing inorganic oxide are formed into pellets at high pressure (e.g., about 350 kPa to about 350,000 kPa), or by co-extrusion, in which a slurry of the molecular sieve and the metal-containing inorganic oxide, optionally together with a separate binder, are forced through a die. If necessary, additional hydrogenating metal can subsequently be deposited on the resultant catalyst composite.

Although the hydroalkylation reaction using an MCM-22 family zeolite catalyst is highly selective towards cyclohexylbenzene, the effluent from the hydroalkylation reaction will likely contain some dicyclohexylbenzene by-product. Depending on the amount of this dicyclohexylbenzene, it may be desirable to either (a) transalkylate the dicyclohexylbenzene with additional benzene or (b) dealkylate the dicyclohexylbenzene to maximize the production of the desired monoalkylated species.

Transalkylation with additional benzene is desirably effected in a transalkylation reactor, separate from the hydroalkylation reactor, over a suitable transalkylation catalyst, such as a molecular sieve of the MCM-22 family, zeolite beta, MCM-68 (see U.S. Pat. No. 6,014,018), zeolite Y, and mordenite. The transalkylation reaction is desirably conducted under at least partial liquid phase conditions, which suitably include a temperature of about 100° C. to about 300° C., a pressure of about 800 kPa to about 3500 kPa, a weight hourly space velocity of about 1 hr$^{-1}$ to about 10 hr$^{-1}$ on total feed, and a benzene/dicyclohexylbenzene weight ratio about of 1:1 to about 5:1.

Dealkylation or cracking is also desirably effected in a reactor separate from the hydroalkylation reactor, such as a reactive distillation unit, at a temperature of about 150° C. to about 500° C. and a pressure of 15 psig to 500 psig (200 kPa to 3550 kPa) over an acid catalyst such as an aluminosilicate, a silicoaluminphosphate, amorphous silica-alumina, an acidic clay, a mixed metal oxide, such as $WO_x/ZrO_2$, phosphoric acid, sulfated zirconia, and mixtures thereof. In certain embodiments, the acid catalyst includes at least one aluminosilicate, or silicoaluminphosphate of the FAU, AEL, AFI, and MWW structural types. Unlike transalkylation, dealkylation can be conducted in the absence of added benzene, although it may be desirable to add benzene to the dealkylation reaction to reduce coke formation. In this case, the weight ratio of benzene to poly-alkylated aromatic compounds in the feed to the dealkylation reaction is desirably from 0 to about 0.9, such as from about 0.01 to about 0.5. Similarly, although the dealkylation reaction can be conducted in the absence of added hydrogen, in certain embodiments, hydrogen is introduced into the dealkylation reactor to assist in coke reduction. Suitable hydrogen addition rates are such that the molar ratio of hydrogen to poly-alkylated aromatic compound in the total feed to the dealkylation reactor is from about 0.01 to about 10.

Another significant by-product of the hydroalkylation reaction is cyclohexane. Although a $C_6$-rich stream comprising cyclohexane and unreacted benzene can be readily removed from the hydroalkylation reaction effluent by distillation, owing to the similarity in the boiling points of benzene and cyclohexane, the $C_6$-rich stream is difficult to further separate by simple distillation. However, some or all of the $C_6$-rich stream can be recycled to the hydroalkylation reactor to provide not only part of the benzene feed but also part of the diluents mentioned above.

In some cases, it may be desirable to supply some of the $C_6$-rich stream to a dehydrogenation reaction zone, where the $C_6$-rich stream is contacted with a dehydrogenation catalyst under dehydrogenation conditions sufficient to convert at least part of the cyclohexane in the $C_6$-rich stream portion to benzene, which again can be recycled to the hydroalkylation reaction. In certain embodiments, the dehydrogenation catalyst comprises (a) a support; (b) a hydrogenation-dehydrogenation component; and (c) an inorganic promoter. Conveniently, the support (a) is selected from the group consisting of silica, a silicate, an aluminosilicate, zirconia, and carbon nanotubes, and preferably comprises silica. Suitable hydrogenation-dehydrogenation components (b) comprise at least one metal selected from Groups 6 to 10 of the Periodic Table of Elements, such as platinum, palladium and compounds and mixtures thereof. Desirably, the hydrogenation-dehydrogenation component is present in an amount from about 0.1 wt % to about 10 wt % of the catalyst. A suitable inorganic promoter (c) comprises at least one metal or compound thereof selected from Group 1 of the Periodic Table of Elements, such as a potassium compound. Desirably, the promoter is present in an amount from about 0.1 wt % to about 5 wt % of the catalyst. Suitable dehydrogenation conditions include a temperature of about 250° C. to about 500° C., a pressure of about atmospheric to about 500 psig (100 kPa to 3550 kPa), a weight hourly space velocity of about 0.2 hr$^{-1}$ to 50 hr$^{-1}$, and a hydrogen to hydrocarbon feed molar ratio of about 0 to about 20.

Other disadvantageous impurities of the hydroalkylation reaction are bicyclohexyl (BCH) and the methylcyclopentylbenzene (MCPB) isomers which, because of the similarity in their boiling points, are difficult to separate from the desired cyclohexylbenzene by distillation. Moreover, although 1,2-methylcyclopentylbenzene (2-MCPB), and 1,3-methylcyclopentylbenzene (3-MCPB) are readily converted in the subsequent oxidation/cleavage steps to the phenol and methylcyclopentanones, which are valuable products, 1,1-methylcyclopentylbenzene (1-MCPB) is substantially inert to the oxidation step and so, if not removed, will build up in the $C_{12}$ stream. Similarly, bicyclohexyl (BCH) can lead to separation problems downstream. Thus, at least part of the hydroalkylation reaction product may be treated with a catalyst under conditions to remove at least 1,1-methylcyclopentylbenzene and/or bicyclohexyl from the product. The catalyst is desirably an acid catalyst, such as an aluminosilicate zeolite, and especially faujasite and the treatment is conducted at a temperature of about 100° C. to about 350° C., such as about 130° C. to about 250° C., for a time of about 0.1 to about 3 hours, such as about 0.1 to about 1 hour. The catalytic treatment is believed to isomerize the 1,1-methylcyclopentylbenzene to the more readily oxidizable 1,2-methylcyclopentylbenzene (2-MCPB), and 1,3-methylcyclopentylbenzene (3-MCPB). The bicyclohexyl is believed to react with benzene present in the hydroalkylation reaction product to produce cyclohexane and more of the desired cyclohexylbenzene according to the following reaction:

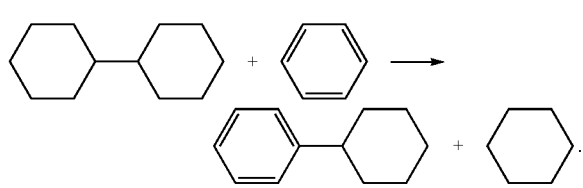

The catalytic treatment can be conducted on the direct product of the hydroalkylation reaction or after distillation of the hydroalkylation reaction product to separate the $C_6$ and/or the heavies fraction.

The cyclohexylbenzene product from the hydroalkylation reaction and any downstream reaction to remove the impurities discussed herein is separated from the reaction effluent(s) and is fed to the oxidation reaction described in more details below.

Cyclohexylbenzene Oxidation

In order to convert the cyclohexylbenzene into phenol and cyclohexanone, the cyclohexylbenzene is initially oxidized to the corresponding hydroperoxide. This is accomplished by contacting the cyclohexylbenzene with an oxygen-containing gas, such as air and various derivatives of air. For example, it is possible to use air that has been compressed and filtered to removed particulates, air that has been compressed and cooled to condense and remove water, or air that has been enriched in oxygen above the natural approximately 21 mol % in air through membrane enrichment of air, cryogenic separation of air or other conventional means.

Suitable oxidation catalysts include N-hydroxy substituted cyclic imides described in U.S. Pat. No. 6,720,462, which is incorporated herein by reference for this purpose. For example, N-hydroxyphthalimide (NHPI), 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3',4,4'-tetracarboxylic diimide), N-hydroxymaleimide, pyridine-2,3-dicarboximide, N-hydroxysuccinimide, N-hydroxy(tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt or N-hydroxy-o-benzenedisulphonimide may be used. Preferably, the catalyst is N-hydroxyphthalimide. Another suitable catalyst is N,N',N"-trihydroxyisocyanuric acid.

These oxidation catalysts can be used either alone or in conjunction with a free radical initiator, and further can be used as liquid-phase, homogeneous catalysts or can be supported on a solid carrier to provide a heterogeneous catalyst. Desirably, the N-hydroxy substituted cyclic imide or the N,N',N"-trihydroxyisocyanuric acid is employed in an amount from 0.0001 wt % to 15 wt %, such as from 0.001 wt % to 5 wt %, of the cyclohexylbenzene.

Suitable conditions for the oxidation step include a temperature from about 70° C. to about 200° C., such as about 90° C. to about 130° C., and a pressure of about 50 kPa to 10,000 kPa. A basic buffering agent may be added to react with acidic by-products that may form during the oxidation. In addition, an aqueous phase may be introduced. The reaction can take place in a batch or continuous flow fashion.

The reactor used for the oxidation reaction may be any type of reactor that allows for introduction of oxygen to cyclohexylbenzene, and may further efficaciously provide contacting of oxygen and cyclohexylbenzene to effect the oxidation reaction. For example, the oxidation reactor may comprise a simple, largely open vessel with a distributor inlet for the oxygen-containing stream. In various embodiments, the oxidation reactor may have means to withdraw and pump a portion of its contents through a suitable cooling device and return the cooled portion to the reactor, thereby managing the exothermicity of the oxidation reaction. Alternatively, cooling coils providing indirect cooling, e.g., by cooling water, may be operated within the oxidation reactor to remove the generated heat. In other embodiments, the oxidation reactor may comprise a plurality of reactors in series, each conducting a portion of the oxidation reaction, optionally operating at different conditions selected to enhance the oxidation reaction at the pertinent conversion range of cyclohexylbenzene or oxygen, or both, in each. The oxidation reactor may be operated in a batch, semi-batch, or continuous flow manner.

Desirably, the product of the cyclohexylbenzene oxidation reaction contains at least 5 wt %, such as at least 10 wt %, for example at least 15 wt %, or at least 20 wt % cyclohexyl-1-phenyl-1-hydroperoxide based upon the total weight of the oxidation reaction effluent. In certain embodiments, the oxidation reaction effluent contains no greater than 80 wt %, or no greater than 60 wt %, or no greater than 40 wt %, or no greater than 30 wt %, or no greater than 25 wt % of cyclohexyl-1-phenyl-1-hydroperoxide based upon the total weight of the oxidation reaction effluent. The oxidation reaction effluent may further comprise imide catalyst and unreacted cyclohexylbenzene. For example, the oxidation reaction effluent may include unreacted cyclohexylbenzene in an amount of at least 50 wt %, or at least 60 wt %, or at least 65 wt %, or at least 70 wt %, or at least 80 wt %, or at least 90 wt %, based upon the total weight of the oxidation reaction effluent.

In addition to the desired cyclohexyl-1-phenyl-1-hydroperoxide, the oxidation step tends to produce certain by-products which, if not removed and/or converted to useful materials would result in loss of valuable feed and/or can adversely influence downstream processes. Among these by-products are phenylcyclohexanols, such as of 2-phenyl-1-cyclohexanol, 3-phenyl-1-cyclohexanol and 4-phenyl-1-cyclohexanol, and phenylcyclohexanones, such as 2-phenylcyclohexanone, 3-phenylcyclohexanone and 4-phenylyclohexanone. Desirably, the phenylcyclohexanols are present in the oxidation reaction effluent in an amount from 0.1 wt % to 10 wt % of the effluent and the phenylcyclohexanones are present in an amount from 0.1 wt % to 5 wt % of the effluent. In the present process, these by-products are removed and converted to useful cyclohexylbenzene, which can then be recycled to the oxidation step. However, as explained below, removal and conversion of these by-products is desirably conducted after the downstream cleavage step.

Hydroperoxide Cleavage

The final reactive step in the conversion of the cyclohexylbenzene into phenol and cyclohexanone involves the acid-catalyzed cleavage of the cyclohexyl-1-phenyl-1-hydroperoxide produced in the oxidation step. Other hydroperoxides that may be present in the oxidation effluent stream may also undergo acid-catalyzed cleavage along with the desired cyclohexyl-1-phenyl-1-hydroperoxide.

In certain embodiments, the acid catalyst used in the cleavage reaction is at least partially soluble in the cleavage effluent, is stable at a temperature of at least 185° C. and has a lower volatility (higher normal boiling point) than cyclohexylbenzene. Desirably, the acid catalyst is also at least partially soluble in the cleavage reaction product. Suitable homogeneous acid catalysts include, but are not limited to, Brønsted acids, Lewis acids, sulfonic acids, perchloric acid, phosphoric acid, hydrochloric acid, p-toluene sulfonic acid, aluminum chloride, oleum, sulfur trioxide, ferric chloride, boron trifluoride, sulfur dioxide, and sulfur trioxide. Sulfuric acid is a preferred acid catalyst.

In various embodiments, the cleavage effluent contains at least 50 weight-parts-per-million (wppm) and no greater than 5000 wppm of the acid catalyst, or at least 100 wppm and no greater than 3000 wppm, or at least 150 wppm and no greater than 2000 wppm of the acid catalyst, or at least 300 wppm and no greater than 1500 wppm of the acid catalyst, based upon the total weight of the cleavage effluent.

In other embodiments, a heterogeneous acid catalyst is employed for the cleavage reaction, such as molecular sieve, and in particular a molecular sieve having a pore size in excess of 7 Å. Examples of suitable molecular sieves include zeolite beta, zeolite Y, zeolite X, ZSM-12, and mordenite. In one embodiment, the molecular sieve comprises a FAU type zeolite having a unit cell size less than 24.35 Å, such as less than or equal to 24.30 Å, even less than or equal to 24.25 Å. The zeolite can be used in unbound form or can be combined with a binder, such as silica or alumina, such that the overall catalyst (zeolite plus binder) comprises from about 20 wt % to about 80 wt % of the zeolite.

The cleavage reaction mixture may contain a polar solvent, such as an alcohol containing less than 6 carbons, such as methanol, ethanol, iso-propanol, and/or ethylene glycol; a nitrile, such as acetonitrile and/or propionitrile; nitromethane; and a ketone containing 6 carbons or less such as acetone, methylethyl ketone, 2- or 3-pentanone, cyclohexanone, and methylcyclopentanone. The preferred polar solvent is phenol and/or cyclohexanone recycled from the cleavage product after cooling. In certain embodiments, the polar solvent is added to the cleavage reaction mixture such that the weight ratio of the polar solvent to the cyclohexylbenzene hydroperoxide in the mixture is in the range of about 1:100 to about 100:1, such as about 1:20 to about 10:1, and the mixture comprises about 10 wt % to about 40 wt % of the cyclohexylbenzene hydroperoxide. The addition of the polar solvent is found not only to increase the degree of conversion of the cyclohexylbenzene hydroperoxide in the cleavage reaction but also to increase the selectivity of the conversion to phenol and cyclohexanone. Although the mechanism is not fully understood, it is believed that the polar solvent reduces the free radical induced conversion of the cyclohexylbenzene hydroperoxide to undesired products such as hexanophenone and phenylcyclohexanol.

In various embodiments, the cleavage reaction mixture includes cyclohexylbenzene in an amount of at least 50 wt %, or at least 60 wt %, or at least 65 wt %, or at least 70 wt %, or at least 80 wt %, or at least 90 wt %, based upon the total weight of the cleavage reaction mixture.

In certain embodiments, the cleavage reaction is conducted under conditions including a temperature of about 20° C. to about 200° C., such as about 40° C. to about 120° C. and a pressure of about 100 kPa to about 2000 kPa, such as about 100 kPa to about 1000 kPa, such that the cleavage reaction mixture is completely or predominantly in the liquid phase during the cleavage reaction.

The reactor used to effect the cleavage reaction may be any type of reactor known to those skilled in the art. For example, the cleavage reactor may be a simple, largely open vessel operating in a near-continuous stirred tank reactor mode, or a simple, open length of pipe operating in a near-plug flow reactor mode. In other embodiments, the cleavage reactor comprises a plurality of reactors in series, each performing a portion of the conversion reaction, optionally operating in different modes and at different conditions selected to enhance the cleavage reaction at the pertinent conversion range. In one embodiment, the cleavage reactor is a catalytic distillation unit.

In various embodiments, the cleavage reactor is operable to transport a portion of the contents through a cooling device and return the cooled portion to the cleavage reactor, thereby managing the exothermicity of the cleavage reaction. Alternatively, the reactor may be operated adiabatically. In one embodiment, cooling coils operating within the cleavage reactor(s) remove any heat generated.

The major product of the cleavage reaction in certain embodiments is a substantially equimolar mixture of phenol and cyclohexanone.

Treatment of Phenylcyclohexanol and Phenylcyclohexanone by-Products

As indicated above the oxidation step produces non-insignificant amount of phenylcyclohexanols and/or phenylcyclohexanones as by-products which, in the present process, are converted to cyclohexylbenzene. Although the conversion of these by-products into cyclohexylbenzene can be conducted directly after the oxidation step, it is more conveniently conducted after the cleavage reaction. In some embodiments, the effluent from cleavage reaction will contain residual sulfuric acid cleavage catalyst in addition to the phenol and cyclohexanone products and the phenylcyclohexanols and/or phenylcyclohexanones by-products. In this case, the residual sulfuric acid in the cleavage reaction effluent is initially neutralized by treating the cleavage effluent with one or more amines or diamines to produce amine salts. The amine salts are then removed from the neutralized cleavage effluent, desirably by an initial distillation step, with the amine salts being removed as heavies. The remainder of the neutralized cleavage effluent can then be further separated, desirably by a further distillation step, into a light fraction containing phenol and cyclohexanone, and a heavy fraction containing the phenylcyclohexanol and/or phenylcyclohexanone by-products. The heavy fraction is then fed together with hydrogen to a reactor containing a bifunctional catalyst comprising a solid acid dehydration component and a hydrogenating metal component. In the reactor, the by-products are dehydrated to phenylcyclohexene, which is then immediately hydrogenated to cyclohexylbenzene. In this way, potential side reactions of the phenylcyclohexene intermediate are minimized, thereby improving catalyst selectivity and stability.

The solid acid dehydration component employed in the bifunctional catalyst used to treat the phenylcyclohexanol and/or phenylcyclohexanone by-products is desirably a molecular sieve, such as zeolite Y, zeolite beta or, more preferably, a member of the MCM-22 family. The hydrogenating metal component of the catalyst desirably comprises at least one metal selected from Groups 6 to 12 of the Periodic Table of Elements, preferably palladium. Conversion of the by-products to cyclohexylbenzene in certain embodiments is conducted at a temperature of 25° C. to 200° C., such as 80° C. to 150° C., and a hydrogen partial pressure of 15 kPa to 1000 kPa, such as 15 kPa to 300 kPa. The cyclohexylbenzene produced can then be recycled to the oxidation stage to enhance the yield of phenol and cyclohexanone.

In some embodiments, it may be desirable to take a vapor or liquid side draw from either the distillation column used to remove the amine salts or from the distillation column used to separate the phenylcyclohexanol and/or phenylcyclohexanone by-products and employ this side draw as a feed to the dehydration/hydrogenation reactor. This would also allow integration of the distillation columns with the dehydration/hydrogenation reactor such that the effluent from the reactor could be fed back into the distillation column(s) to remove impurities produced in the dehydration/hydrogenation reaction.

The invention will now be more particularly described with reference to the following non-limiting examples.

Example 1

Into a clean dry stainless steel tubular reactor having an internal diameter of ⅜ inch (0.95 cm) was charged 0.5 grams of a commercial zeolite Y catalyst diluted with 4.5 ml of 20/40 mesh quartz. The tubular reactor was filled with additional 20/40 mesh quartz and was placed within the heated zone of a fixed bed reactor. A reaction mixture having the composition given in TABLE I below was introduced to the fixed bed reactor at temperature 100° C. and at 2 hr$^{-1}$ WHSV:

TABLE I

| Component | Amount | |
| --- | --- | --- |
| | (gram) | (mole) |
| 1,2,4-trimethylbenzene (as a solvent) | 988 | 8.22 |
| Pentadecane (as an internal standard) | 87.9 | 0.414 |
| 1-phenyl-1-cyclohexene | 8.0 | 0.051 |
| 6-hydroxylhexaphenone | 4.6 | 0.024 |
| 2-phenyl-1-cyclohexanol | 1.1 | 0.0063 |
| 4-phenyl-1-cyclohexanol | 5.0 | 0.0284 |
| 2-phenylcyclohexanone | 0.94 | 0.0054 |
| 4-phenylcyclohexanone | 4.92 | 0.028 |

Figure 2:
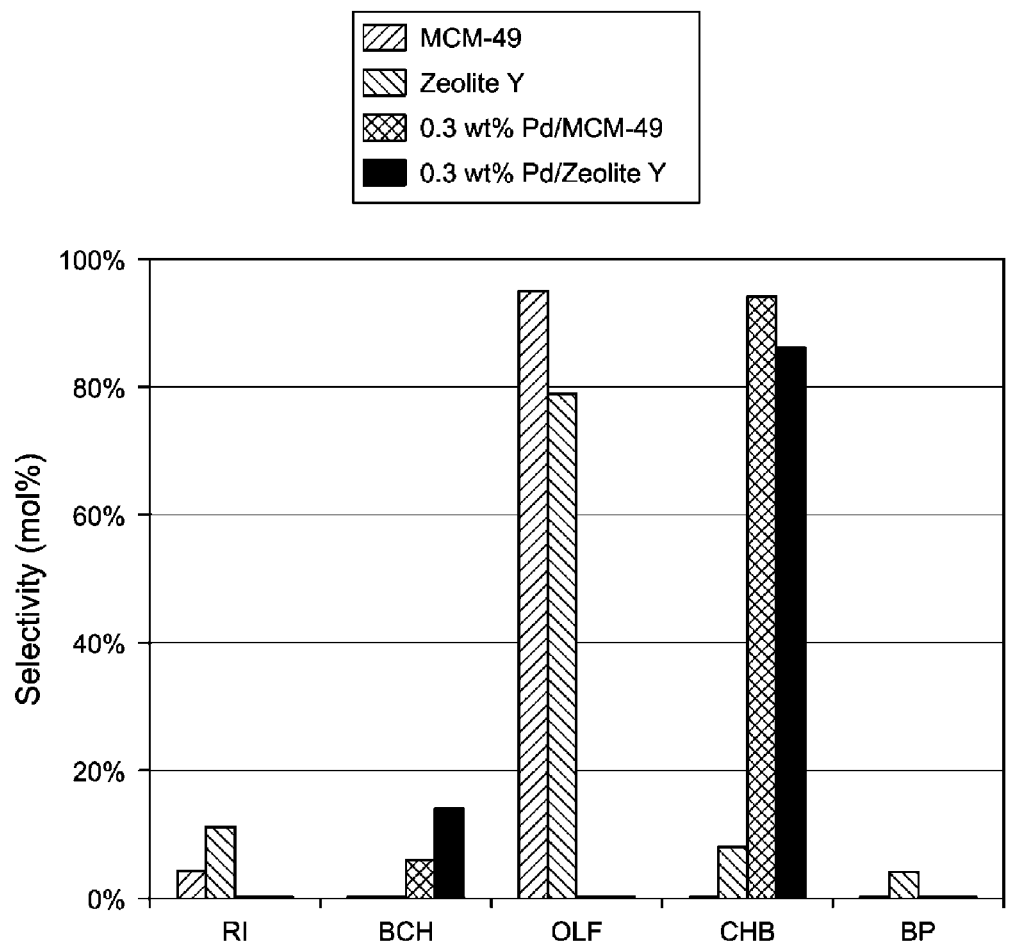
FIG. 2 is a graph comparing the product selectivity of the processes of Examples 1 to 4.

The conversion of the phenylcyclohexanol (2-phenyl-1-cyclohexanol and 4-phenyl-1-cyclohexanol) in wt % against time on stream (T.O.S.) in hours is shown in FIG. 1 as curve 105. The selectivity to different products, namely ring isomers (phenyl methyl cyclopentenes, RI), bicyclohexane (BCH), olefins (OLF), cyclohexylbenzene (CHB) and biphenyl (BP), in mol %, is shown in FIG. 2.

Example 2

The process of Example 1 was repeated but with the catalyst being a 80 wt % MCM-49/20 wt % alumina extrudate cut into ½₀ inch (0.13 cm) long pellets. Again the conversion of the phenylcyclohexanol in wt % against time on stream in hours is shown in FIG. 1 as curve 107 and the product selectivity is shown in FIG. 2.

Example 3

The process of Example 2 was repeated but with the MCM-49/alumina having been combined with 0.3 wt % Pd by incipient wetness impregnation and with the reaction mixture being introduced to the reactor at a WHSV of 10 hr$^{-1}$ together with a hydrogen co-feed at a flow rate 170 cc/min. Again the conversion of the phenylcyclohexanol in wt % against time on stream is shown in FIG. 1 as curve 103 and the product selectivity is shown in FIG. 2.

Example 4

The process of Example 1 was repeated but with the zeolite Y catalyst having been combined with 0.3 wt % Pd by incipient wetness impregnation and with the reaction mixture being introduced to the reactor at a WHSV of 10 together with a hydrogen co-feed at a flow rate 170 cc/min. Again the conversion of the phenylcyclohexanol in wt % against time on stream is shown in FIG. 1 as curve 101 and the product selectivity is shown in FIG. 2.

It will be seen from FIG. 1 that the processes of Examples 3 and 4 (using the Pd impregnated catalysts with hydrogen co-feed) were run at essentially 100% conversion for more than 300 hours on stream substantially without any catalyst deactivation. In contrast, in the processes of Examples 1 and 2 (catalysts without Pd and no hydrogen co-feed), the catalysts showed rapid deactivation and, especially in the case of Example 2, lower initial alcohol conversion.

In addition, it will be seen from FIG. 2 that the processes of Examples 3 and 4 exhibited high selectivity to cyclohexylbenzene, with the only measurable by-product being bicyclohexane. In contrast, in the processes of Examples 1 and 2, the main reaction products were olefins together with measurable quantities of ring isomers and biphenyl.

Example 5

Figure 3:
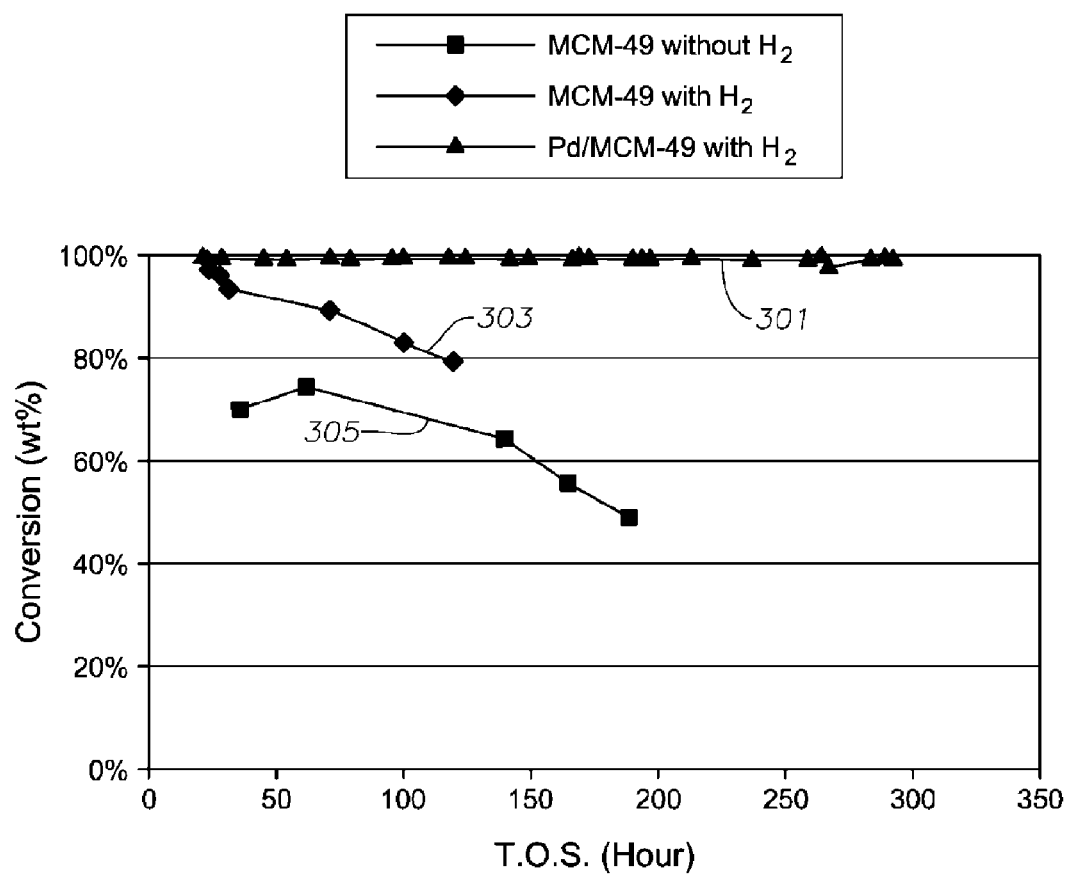
FIG. 3 is a graph comparing phenylcyclohexanol conversion against time on stream for the processes of Examples 2, 3 and 5.

The process of Example 2 (MCM-49/alumina with no Pd) was repeated but with a hydrogen co-feed at a flow rate 170 cc/min. The conversion of the phenylcyclohexanol in wt % against time on stream is shown as curve 303 in FIG. 3, which also shows the results obtained in Example 2 (no hydrogen as curve 305) and Example 3 (MCM-49/alumina with Pd and hydrogen co-feed as curve 301). It will be seen from FIG. 3 that, in the absence of Pd on the catalyst, co-feeding hydrogen did not prevent catalyst deactivation.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention. The contents of all references mentioned herein are incorporated by reference in their entirety.

The invention claimed is:

1. A process for producing phenol and/or cyclohexanone, said process comprising:
   (a) contacting cyclohexylbenzene with an oxygen-containing gas under conditions effective to produce an oxidation effluent containing cyclohexylbenzene hydroperoxide;
   (b) contacting at least part of said oxidation effluent containing cyclohexylbenzene hydroperoxide with a cleavage catalyst under conditions effective to produce a cleavage effluent containing phenol and cyclohexanone;
   wherein at least one of said oxidation effluent and said cleavage effluent contains at least one by-product selected from phenylcyclohexanols and phenylcyclohexanones;
   (c) contacting at least part of said at least one effluent containing said at least one by-product with a dehydration catalyst under conditions effective to convert at least part of said by-product to phenylcyclohexene; and
   (d) contacting at least part of said phenylcyclohexene with hydrogen under conditions effective to convert at least part of said phenylcyclohexene to cyclohexylbenzene,
   wherein said contacting (c) and contacting (d) are conducted in the same reaction zone in the presence of a bifunctional catalyst comprising (i) an acid dehydration component comprising a molecular sieve of the MCM-22 family, and (ii) a hydrogenating metal component.

2. The process of claim 1, wherein said hydrogenating metal component comprises at least one metal selected from Groups 6 to 12 of the Periodic Table of Elements.

3. The process of claim 1, wherein said hydrogenating metal component comprises palladium.

4. The process of claim 1, wherein said bifunctional catalyst comprises from 0.1 wt % to 1.0 wt % of said hydrogenating metal component.

5. The process of claim 1, wherein said conditions in said contacting steps (c) and (d) comprise a temperature of 25° C. to 200° C.

6. The process of claim 1, wherein said conditions in said contacting step (d) comprise a hydrogen partial pressure of 15 kPa to 1000 kPa.

7. The process of claim 1, wherein said at least one by-product comprises at least one of 2-phenyl-1-cyclohexanol, 3-phenyl-1-cyclohexanol, 4-phenyl-1-cyclohexanol, 2-phenylcyclohexanone, 3-phenylcyclohexanone, and 4-phenylcyclohexanone.

8. The process of claim 1, further comprising:
(e) separating at least part of said cleavage effluent from said contacting step (b) into a first fraction containing phenol and cyclohexanone and a second fraction containing said at least one by-product; and
(f) supplying said second fraction to said contacting step (c).

9. The process of claim 8, wherein said separating step (e) is effected in a first distillation column.

10. The process of claim 9, wherein said second fraction is removed as a side stream from said first distillation column.

11. The process of claim 9, wherein at least part of the product produced in said contacting step (d) is fed back to said first distillation column.

12. The process of claim 8, wherein said cleavage catalyst in said contacting step (b) comprises sulfuric acid and said process further comprises:
(g) neutralizing a residual sulfuric acid in said cleavage effluent with amines to produce amine salts in said cleavage effluent; and
(h) removing at least part of said amine salts prior to said separating step (e).

13. The process of claim 12, wherein said removing step (h) is effected in a second distillation column.

14. The process of claim 1, further comprising:
(i) recycling at least part of said cyclohexylbenzene produced in said contacting step (d) to said contacting step (a).

15. The process of claim 1, wherein said contacting step (a) is effected in the presence of a catalyst.

16. The process of claim 1, wherein said contacting step (a) is effected in the presence of a cyclic imide catalyst.

17. The process of claim 1, wherein said cyclohexylbenzene is produced by alkylation of benzene with cyclohexene.

18. The process of claim 1, wherein said cyclohexylbenzene is produced by a reaction of benzene with hydrogen in the presence of a hydroalkylation catalyst.

19. A process for producing phenol and/or cyclohexanone, said process comprising:
(I) contacting benzene with hydrogen in the presence of a hydroalkylation catalyst under a hydroalkylation condition effective to produce a hydroalkylation effluent comprising cyclohexylbenzene;
(II) contacting at least part of said cyclohexylbenzene in said hydroalkylation effluent with an oxygen-containing gas under conditions effective to produce an oxidation effluent containing cyclohexylbenzene hydroperoxide;
(III) contacting at least part of said oxidation effluent containing cyclohexylbenzene hydroperoxide with a cleavage catalyst under conditions effective to produce a cleavage effluent containing phenol and cyclohexanone,
wherein at least one of said oxidation effluent and said cleavage effluent contains at least one by-product selected from phenylcyclohexanols and phenylcyclohexanones;
(IV) contacting at least part of said at least one effluent containing said at least one by-product with a dehydration catalyst under conditions effective to convert at least part of said by-product to phenylcyclohexene; and
(V) contacting at least part of said phenylcyclohexene with hydrogen under conditions effective to convert at least part of said phenylcyclohexene to cyclohexylbenzene;
wherein said contacting (IV) and said contacting (V) are conducted in the presence of a bifunctional catalyst comprising (i) an acid dehydration component comprising a molecular sieve of the MCM-22 family, and (ii) a hydrogenating metal component.

20. The process of claim 19, further comprising:
(VI) recycling at least part of said cyclohexylbenzene produced in step (V) to said contacting step (II).

21. The process of claim 19, further comprising:
(VII) separating at least part of said cleavage effluent produced in said contacting step (III) into a first fraction containing phenol and cyclohexanone and a second fraction containing said at least one by-product; and
(VIII) supplying at least part of said second fraction to said contacting step (IV).

* * * * *